(12) United States Patent
Heberle et al.

(10) Patent No.: US 9,513,343 B2
(45) Date of Patent: Dec. 6, 2016

(54) MEASURING SYSTEM

(71) Applicant: Micronas GmbH, Freiburg (DE)

(72) Inventors: Klaus Heberle, Emmendingen (DE);
Joerg Franke, Freiburg (DE); Oliver Breitwieser, Gundelfingen (DE); Timo Kaufmann, Waldkirch-Suggental (DE)

(73) Assignee: Micronas GmbH, Freiburg (DE)

( * ) Notice: Subject to any disclaimer, the term of this patent is extended or adjusted under 35 U.S.C. 154(b) by 270 days.

(21) Appl. No.: 14/272,837

(22) Filed: May 8, 2014

(65) Prior Publication Data

US 2014/0333298 A1 Nov. 13, 2014

(30) Foreign Application Priority Data

May 8, 2013 (DE) .................. 10 2013 007 902

(51) Int. Cl.

| G01N 27/72 | (2006.01) |
|---|---|
| G01R 33/12 | (2006.01) |
| G01R 33/00 | (2006.01) |
| G01V 3/08 | (2006.01) |
| G01D 5/14 | (2006.01) |

(52) U.S. Cl.
CPC ........... *G01R 33/0017* (2013.01); *G01N 27/72* (2013.01); *G01R 33/1215* (2013.01); *G01V 3/08* (2013.01); *G01D 5/145* (2013.01)

(58) Field of Classification Search
CPC ........ G01N 27/72; G01R 33/1215; G01V 3/08
USPC ........................................ 324/228
See application file for complete search history.

(56) References Cited

U.S. PATENT DOCUMENTS

| 5,781,005 | A | 7/1998 | Vig et al. |
|---|---|---|---|
| 5,963,028 | A | 10/1999 | Engel et al. |
| 6,265,865 | B1 | 7/2001 | Engel et al. |
| 6,278,269 | B1 | 8/2001 | Vig et al. |
| 6,577,123 | B2 | 6/2003 | Schroeder et al. |
| 6,922,052 | B2 | 7/2005 | Steinruecken et al. |
| 7,002,333 | B2 | 2/2006 | Blasco Claret et al. |
| 7,119,539 | B2 * | 10/2006 | Butzmann ............ G01R 33/096 324/207.21 |
| 7,250,760 | B2 | 7/2007 | Ao |

(Continued)

FOREIGN PATENT DOCUMENTS

| CH | 682 349 A5 | 8/1993 |
|---|---|---|
| CN | 1426530 A | 6/2003 |

(Continued)

*Primary Examiner* — Reena Aurora
(74) *Attorney, Agent, or Firm* — Muncy, Geissler, Olds & Lowe, P.C.

(57) ABSTRACT

A measuring system having a magnetic device for generating a magnetic field and having a magnetic field sensor for detecting a flux density of the magnetic field at least in a first spatial direction, whereby the magnetic field sensor is fixedly positioned relative to the magnetic device. The magnetic device has at least two main poles for generating a main magnetic field and at least two secondary poles for generating a secondary magnetic field. The magnetic field in the magnetic field sensor is formed by superposition of the main magnetic field and the secondary magnetic field. The magnetic field sensor is designed to measure the flux density of the superposition in the first spatial direction, and, in the magnetic field sensor, the secondary magnetic field compensates at least partially the main magnetic field in the first spatial direction.

13 Claims, 3 Drawing Sheets

(56) References Cited

U.S. PATENT DOCUMENTS

| | | |
|---|---|---|
| 7,504,824 B2 | 3/2009 | Crolly et al. |
| 8,193,805 B2 | 6/2012 | Kasajima |
| 8,680,847 B2 | 3/2014 | Franke et al. |
| 8,717,010 B2 | 5/2014 | Ausserlechner et al. |
| 9,000,763 B2 | 4/2015 | Ausserlechner |
| 2002/0180427 A1* | 12/2002 | Schroeder .............. G01D 5/147 324/207.24 |
| 2006/0066295 A1 | 3/2006 | Tamura et al. |
| 2009/0284201 A1 | 11/2009 | Jeung |
| 2011/0291650 A1 | 12/2011 | Franke et al. |
| 2012/0217960 A1 | 8/2012 | Ausserlechner |

FOREIGN PATENT DOCUMENTS

| | | |
|---|---|---|
| CN | 1675851 A | 9/2005 |
| CN | 1930451 A | 3/2007 |
| CN | 101587174 A | 11/2009 |
| CN | 102027659 A | 4/2011 |
| CN | 102062807 A | 5/2011 |
| CN | 102650683 A | 8/2012 |
| CN | 102954807 A | 3/2013 |
| DE | 100 09 173 A1 | 9/2001 |
| DE | 698 27 559 T2 | 12/2005 |
| DE | 10 2012 203 001 A1 | 8/2012 |
| WO | WO 2010/060607 A2 | 6/2010 |

\* cited by examiner

MEASURING SYSTEM

This nonprovisional application claims priority under 35 U.S.C. §119(a) to German Patent Application No. 10 2013 007 902.0, which was filed in Germany on May 8, 2013, and which is herein incorporated by reference.

BACKGROUND OF THE INVENTION

Field of the Invention

The present invention relates to a measuring system.

Description of the Background Art

WO 2010/060607 A2, which corresponds to U.S. Pat. No. 8,680,847, discloses an IC package with a semiconductor chip with an integrated circuit and an integrated magnetic sensor. A permanent magnet, whose magnetic flux penetrates the sensor, is spaced apart from the semiconductor chip package. If an object to be measured approaches the head end of the semiconductor chip, the magnetic flux density through the sensor changes.

U.S. Pat. No. 7,250,760 B2 discloses integrated magnetic Hall sensors in which a permanent magnet is disposed in the IC package. In this case, the Hall sensors are arranged in such a way to the field of the permanent magnet that a Hall voltage is generated without an external field effect.

DE 698 27 559 T2, which corresponds to U.S. Pat. Nos. 5,963,028 and 6,265,865, discloses a package for a magnetic field sensor. Typically, an air gap is defined as the distance between an exciter and the outer surface of the package, which contains a sensing element of the magnetic field sensor. An "effective air gap" can be described as the distance between the exciter and the sensing element itself. Magnetic field sensors typically contain a permanent magnet and a sensing element, which is encapsulated in a package. This package type, however, is not suitable for harsh environments, particularly those in an automobile. Therefore, sensing elements packaged in such a way are enclosed further in an additional package (overmold), which provides protection from moisture and dirt. This results in a decrease in the peak magnetic field strength, as a tooth passes through the magnetic field in proximity to the sensor element. It is desirable in DE 698 27 559 T2 to have the sensor element as close as possible to the magnet, because the magnetic field decreases as a function of the air gap. A smaller distance allows the use of a small magnet with a lower energy product.

DE 10 2012 203 001 A1, which corresponds to U.S. 2012/0217960, discloses a 3-D magnetic sensor. The magnetic field sensor has a flat soft-magnetic body, which is arranged on a surface of a substrate, which has a magnetic sensor array having a plurality of spatially diverse magnetic sensor elements, disposed in a predetermined configuration. In the presence of an external magnetic field, the flat soft-magnetic body is magnetized to generate a reactionary magnetic field. The plurality of magnetic sensor elements are each configured to measure a magnetic field value of a superposition of the external magnetic field and of the reactionary magnetic field along a first axis (e.g., a z-axis), which results in a plurality of spatially diverse measurements of the magnetic field component along the first axis. The plurality of spatially diverse measurements can be used to compute magnetic field components of the external magnetic field along a plurality of axes (e.g., x-axis, y-axis, and z-axis).

SUMMARY OF THE INVENTION

It is therefore an object of the invention to improve a measuring system.

Accordingly, in an embodiment, a measuring system is provided having a magnetic device for generating a magnetic field and having a magnetic field sensor for detecting a flux density of the magnetic field at least in a first spatial direction. The magnetic field sensor is fixedly positioned relative to the magnetic device.

The magnetic device can have at least two main poles for generating a main magnetic field and at least two secondary poles for generating a secondary magnetic field.

The magnetic field in the magnetic field sensor can be formed by superposition of the main magnetic field and the secondary magnetic field.

The magnetic field sensor can be designed to measure the flux density of the superposition in the first spatial direction.

In the magnetic field sensor the secondary magnetic field can compensate at least partially the main magnetic field in the first spatial direction.

Tests by the applicant have shown that it is possible to modify the magnetic field of a magnet, so that, in comparison with an original, state without modification, it has a magnetic flux density component clearly reduced at specific points within the space for magnetic field sensors. This flux density component occurs as an offset in the output signal of the magnetic field sensor. The reduction of this offset therefore increases the signal-to-offset ratio. The reduction of the magnetic flux density component in the present case is achieved by more than two magnetic poles.

According to an embodiment, it is provided that the magnetic device has a first permanent magnet with the two main poles for generating the main magnetic field and a second permanent magnet with the two secondary poles for generating the secondary magnetic field.

According to an embodiment, it is provided that the second permanent magnet has a polarity opposite to the first permanent magnet.

According to an embodiment, it is provided that the second permanent magnet has smaller dimensions than the first permanent magnet. Preferably, the second permanent magnet is arranged centered relative to the first permanent magnet.

According to an embodiment, it is provided that the magnetic device has only one first permanent magnet with the two main poles for generating the main magnetic field. The first permanent magnet has at least one recess with the two secondary poles for generating the secondary magnetic field.

According to an embodiment, it is provided that pole surfaces of the secondary poles are formed parallel to the pole surfaces of main poles.

According to an embodiment, it is provided that pole surfaces of the secondary poles are formed not parallel but at an angle to the pole surfaces of the main poles.

According to an embodiment, the measuring system has an encoder for changing a flux density in the first spatial direction in the area of the magnetic field sensor.

According to an embodiment, it is provided that the magnetic device and the magnetic field sensor are integrated in a component package. The component package is made for mounting on a circuit substrate.

The previously described refinement variants are especially advantageous both individually and in combination. In this regard, all refinement variants can be combined with one another. Some possible combinations are explained in the description of the exemplary embodiments shown in the figures. These possible combinations of the refinement variants, depicted therein, are not definitive, however.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
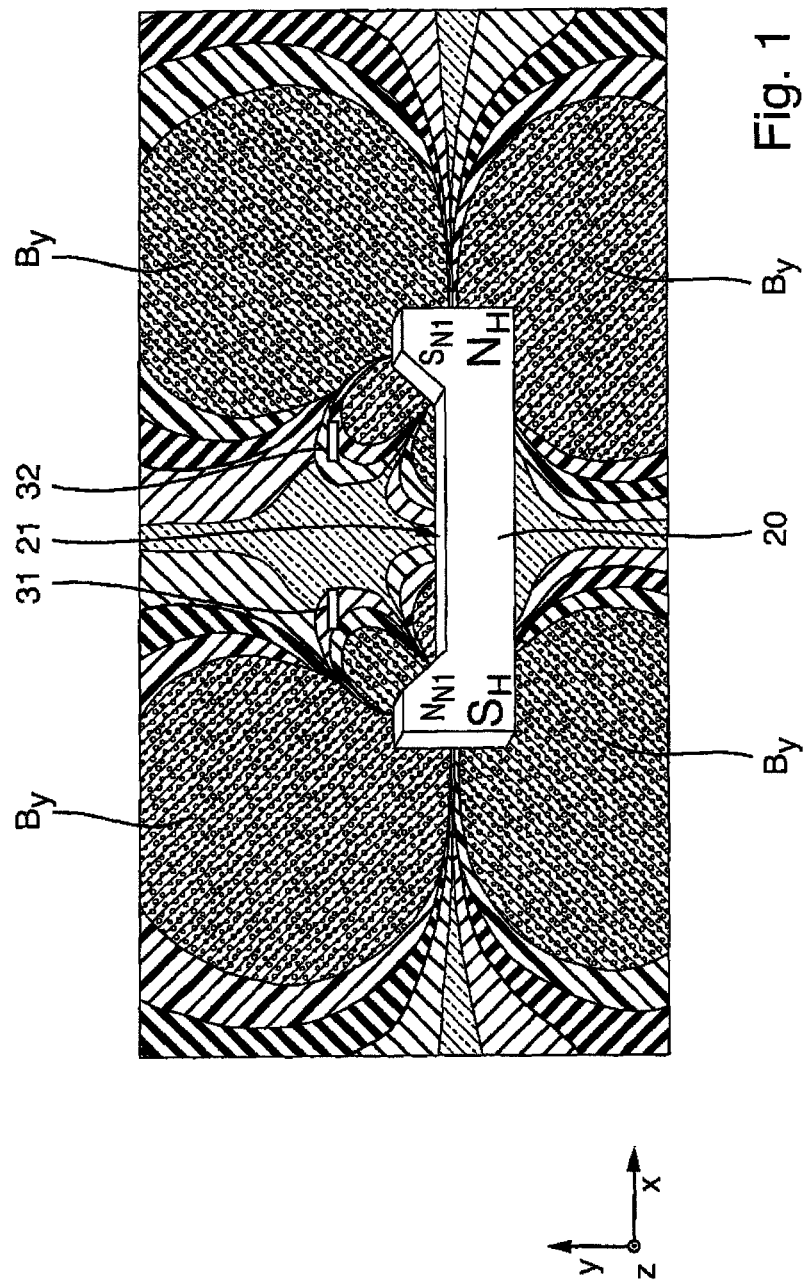
FIG. 1 is a schematic sectional view of an exemplary embodiment of a measuring system with a magnetic device and magnetic field sensors.

A schematic sectional view through a measuring system is shown in FIG. 1. The measuring system has a magnetic device 20 for generating a magnetic field and two magnetic field sensors 31, 32. Magnetic device 20 is a specially designed permanent magnet 20. Magnetic field sensors 31, 32 are fixedly positioned relative to magnetic device 20, 50, 60, for example, by plastic by means of a form closure. In addition, a coordinate system with the spatial directions x, y, and z is shown in FIG. 1. Furthermore, the y-component By of magnetic flux B in spatial direction y is shown in FIG. 1. The illustration of the y-component By in FIG. 1 is determined here by means of FEM simulation. FIG. 1 here shows the y-component By in the case that no encoder made of a ferromagnetic material influences the magnetic field. The aim of the exemplary embodiment of FIG. 1 is to achieve the smallest possible value of the y-component By of the magnetic flux B in the spatial direction y in the area of each magnetic field sensor 31, 32 without an encoder, and with an encoder a clearly higher value of the y-component By of the magnetic flux B in the spatial direction y in the area of each magnetic field sensor 31, 32.

Permanent magnet 20 on its front surfaces has two main poles $N_H$, $S_H$ for generating a main magnetic field. Permanent magnet 20 is magnetized in the x-direction. Secondary poles $S_{N1}$, $N_{N1}$ arise by means of a notch 21 in permanent magnet 20. Secondary poles $N_{N1}$, $S_{N1}$ generate a secondary magnetic field. Pole surfaces of secondary poles $N_{N1}$, $S_{N1}$ are thereby formed at an angle of about 45° to the pole surfaces of main poles $N_H$, $S_H$ and therefore not parallel to the pole surfaces of main poles $N_H$, $S_H$. Alternatively, secondary poles $N_{N1}$, $S_{N1}$ can also be formed at an angle or parallel to the pole surfaces of main poles $N_H$, $S_H$.

In magnetic field sensors 31, 32, the secondary magnetic field and the main magnetic field overlap. In the exemplary embodiment of FIG. 1, the secondary magnetic field is weaker than the main magnetic field. The secondary magnetic field and the main magnetic field also overlap in magnetic field sensors 31, 32. It is shown in the exemplary embodiment of FIG. 1 that in the spatial direction y in the area of magnetic field sensors 31, 32 the y-component By of the magnetic flux density without the presence of an encoder is especially low because of the superposition. The flux density is therefore significantly reduced compared with a magnetic device 20 without the two secondary poles $N_{N1}$, $S_{N1}$.

Basically, a single magnetic field sensor 31, 32 is sufficient for detecting the flux density By of the magnetic field in the spatial direction y. In the exemplary embodiment of FIG. 1, two magnetic field sensors 31, 32 are provided, which are operated differentially. Both magnetic field sensors 31, 32 detect the y-component By of the magnetic flux density, whereby the y-component By in both magnetic field sensors 31, 32 has a different sign.

Tests by the applicant have shown that the signal-to-offset ratio can be increased sixfold by the superposition of the main magnetic field and secondary magnetic field.

Figure 2:
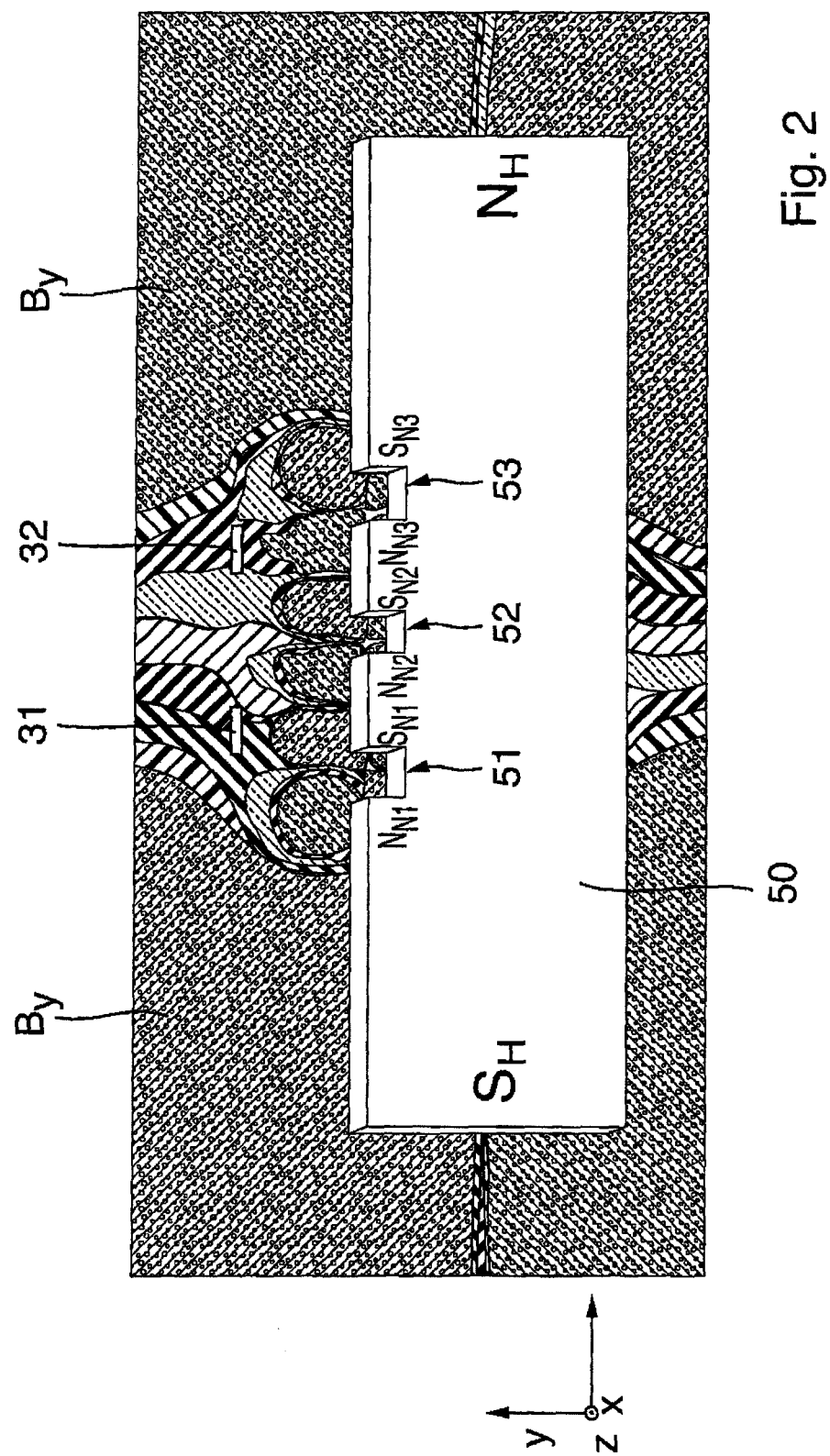
FIG. 2 is a schematic sectional view of an exemplary embodiment of a measuring system with a magnetic device and magnetic field sensors.

A second exemplary embodiment of a measuring system is shown in FIG. 2 as a schematic sectional view. Magnetic device 50 has a permanent magnet 50 with three indentations 51, 52, 53. Secondary poles $N_{N1}$, $S_{N1}$, $N_{N2}$, $S_{N2}$, $N_{N3}$, $S_{N3}$ are formed by indentations 51, 52, 53. A secondary magnetic field of secondary poles $N_{N1}$, $S_{N1}$, $N_{N2}$, $S_{N2}$, $N_{N3}$, $S_{N3}$ again overlaps a main magnetic field of both main poles $N_H$ and $S_H$. Two magnetic field sensors 31, 32 in the exemplary embodiment of FIG. 2 are made as Hall sensors. Both magnetic field sensors 31, 32 are designed to measure the flux density By of the superposition in the first spatial direction y. The flux density By in the area of magnetic field sensors 31, 32 in this regard is significantly reduced by the compensation compared with a magnetic device without these secondary poles $N_{N1}$, $S_{N1}$, $N_{N2}$, $S_{N2}$, $N_{N3}$, $S_{N3}$.

Figure 3:
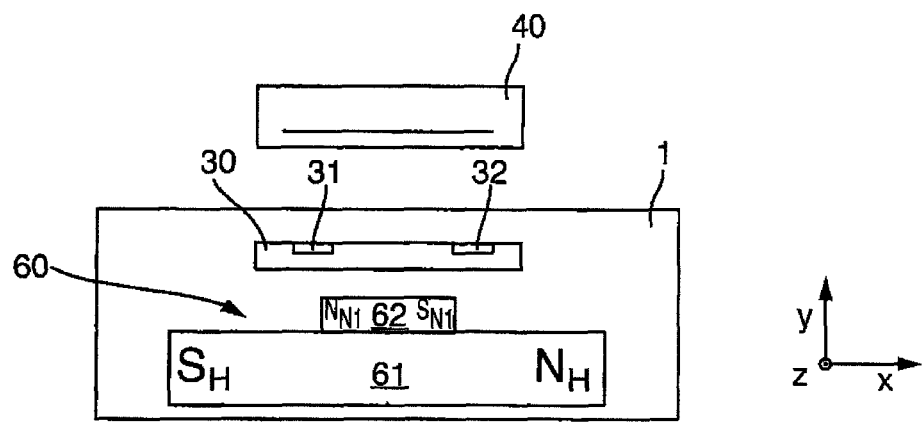
FIG. 3 is a schematic sectional view of an exemplary embodiment of a measuring system with a magnetic device and magnetic field sensors.

A further exemplary embodiment with a magnetic device 60 with two permanent magnets 61, 62 is shown schematically in a sectional view in FIG. 3. Also shown is an encoder 40 for deflecting magnetic field lines of magnetic device 60, whereby the deflection causes a change in the flux density By in magnetic field sensors 31, 32. Magnetic device 60 therefore has a first permanent magnet 61 with the two main poles $N_H$, $S_H$ for generating a main magnetic field and a second permanent magnet 62 with two secondary poles $N_{N1}$, $S_{N1}$ for generating a secondary magnetic field.

In the exemplary embodiment of FIG. 3, second permanent magnet 62 is made smaller than first permanent magnet 61. Second permanent magnet 62 is magnetized opposite to first permanent magnet 61.

It is shown in the exemplary embodiment of FIG. 3 that magnet device 60 and magnetic field sensors 31, 32 are integrated in a component package 1. Component package 1 is made for mounting on a circuit substrate, for example, a circuit board (not shown). For example, magnet device 60 and a semiconductor chip 30, having magnetic field sensors 31, 32, are integrated, for example, with an integrated circuit, in a plastic package 1.

The invention is not limited to the shown embodiment variants in FIGS. 1 through 3. For example, it is possible to achieve a decrease in the offset with non-straight magnetization directions of a permanent magnet. Likewise, as a departure from the exemplary embodiments in FIGS. 1 to 3, it is possible to arrange the magnetic field sensors within the indentations in the permanent magnet, for example, in notch 21 of the exemplary embodiment of FIG. 1. The functionality of the measuring system according to FIG. 1 can be used especially advantageously for rotation measurement by means of a rotating encoder.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A measuring system comprising:
   a fixed magnetic device including a first permanent magnet for generating a magnetic field, the first permanent magnet having a main extension surface along a second spatial direction and at least two magnetic protrusions opposite the main extension surface, the at least two magnetic protrusions extending in a third spatial direction to a protrusion plane, the third spatial direction being perpendicular to the second spatial direction, and the protrusion plane being parallel to the main extension surface; and
   a magnetic field sensor for detecting a flux density of the magnetic field at least in a first spatial direction, the magnetic field sensor being fixedly positioned further from the main extension surface than the protrusion plane, and offset by a distance from the protrusion plane of the magnetic device,
   wherein the magnetic device has at least two main poles for generating a main magnetic field and at least two secondary poles for generating a secondary magnetic field,
   wherein the magnetic field in the magnetic field sensor is formed by superposition of the main magnetic field and the secondary magnetic field,
   wherein the magnetic field sensor is configured to measure the flux density of the superposition in the first spatial direction, and
   wherein, in the magnetic field sensor, the secondary magnetic field compensates at least partially the main magnetic field in the first spatial direction.

2. The measuring system according to claim 1, wherein the magnetic device has a first permanent magnet with two main poles for generating the main magnetic field, and wherein the two secondary poles for generating the secondary magnetic field disposed at lateral ends of the at least one recess.

3. The measuring system according to claim 1, wherein pole surfaces of the secondary poles are formed parallel to the pole surfaces of the main poles.

4. The measuring system according to claim 1, wherein pole surfaces of the secondary poles are formed at an angle to the pole surfaces of the main poles.

5. The measuring system according to claim 1, further comprising an encoder for changing a flux density in the first spatial direction in an area of the magnetic field sensor.

6. The measuring system according to claim 1, wherein the magnetic device and the magnetic field sensor are integrated in a component package, and wherein the component package is made for mounting on a circuit substrate.

7. The measuring system according to claim 1, wherein the two main poles are disposed at opposite ends of the main extension surface.

8. The measuring system according to claim 1, wherein the two magnetic protrusions are disposed at opposite ends of the first permanent magnet, wherein each magnetic protrusion includes a face parallel to the protrusion plane, and wherein the polarity of the face of each magnetic protrusion is opposite that of a nearest one of the at least two main poles.

9. The measuring system according to claim 1, wherein the at least two secondary poles are disposed on the at least two protrusions, and wherein the at least two main poles are disposed at opposite ends of the extension surface.

10. The measuring system according to claim 1, wherein the at least two main poles are disposed along the second spatial direction, and wherein the at least two secondary poles are disposed along the third spatial direction.

11. A measuring system comprising:
    a magnetic device for generating a magnetic field; and
    a magnetic field sensor for detecting a flux density of the magnetic field at least in a first spatial direction, the magnetic field sensor being fixedly positioned relative to the magnetic device,
    wherein the magnetic device has at least two main poles for generating a main magnetic field and at least two secondary poles for generating a secondary magnetic field,
    wherein the magnetic field in the magnetic field sensor is formed by superposition of the main magnetic field and the secondary magnetic field,
    wherein the magnetic field sensor is configured to measure the flux density of the superposition in the first spatial direction,
    wherein, in the magnetic field sensor, the secondary magnetic field compensates at least partially the main magnetic field in the first spatial direction,
    wherein the magnetic device has a first permanent magnet with the two main poles for generating the main magnetic field and a second permanent magnet with the two secondary poles for generating the secondary magnetic field,
    wherein the second permanent magnet has a polarity opposite to the first permanent magnet, and
    wherein the second permanent magnet has smaller dimensions than the first permanent magnet.

12. The measuring system according to claim 11, wherein a first extension direction of the first permanent magnet is along a first longitudinal axis of the first permanent magnet, wherein a second extension direction of the second permanent magnet is along a second longitudinal axis of the second permanent magnet, and wherein the first extension direction and second extension direction are parallel.

13. The measuring system according to claim 12, wherein the second permanent magnet is disposed on the first permanent magnet, and wherein the second permanent magnet is arranged between the first permanent magnet and the magnetic field sensor.

* * * * *